(12) United States Patent
Swain

(10) Patent No.: US 8,597,286 B2
(45) Date of Patent: Dec. 3, 2013

(54) DEVICE, SYSTEM AND METHOD FOR IN-VIVO CAUTERIZATION

(75) Inventor: Christopher Paul Swain, London (GB)

(73) Assignee: Given Imaging Ltd, Yoqneam (IL)

(*) Notice: Subject to any disclaimer, the term of this patent is extended or adjusted under 35 U.S.C. 154(b) by 1134 days.

(21) Appl. No.: 11/665,122

(22) PCT Filed: Oct. 11, 2005

(86) PCT No.: PCT/IL2005/001081
§ 371 (c)(1),
(2), (4) Date: Jul. 6, 2009

(87) PCT Pub. No.: WO2006/040768
PCT Pub. Date: Apr. 20, 2006

(65) Prior Publication Data
US 2009/0299359 A1    Dec. 3, 2009

Related U.S. Application Data

(63) Continuation of application No. PCT/IL2005/000510, filed on May 17, 2005.

(60) Provisional application No. 60/617,057, filed on Oct. 12, 2004, provisional application No. 60/632,260, filed on Dec. 2, 2004.

(30) Foreign Application Priority Data

Oct. 11, 2004   (IL) .......................................... 164501

(51) Int. Cl.
*A61B 18/08*   (2006.01)
*A61B 18/06*   (2006.01)

(52) U.S. Cl.
USPC ............................................................ 606/27

(58) Field of Classification Search
USPC ............................................. 606/27, 41, 49
See application file for complete search history.

(56) References Cited

U.S. PATENT DOCUMENTS

| | | |
|---|---|---|
| 3,228,400 A | 1/1966 | Armao |
| 3,369,549 A | 2/1968 | Armao |
| 4,278,077 A | 7/1981 | Mizumoto |

(Continued)

FOREIGN PATENT DOCUMENTS

| | | |
|---|---|---|
| DE | 344 0177 | 5/1986 |
| JP | 57-45833 | 3/1982 |

(Continued)

OTHER PUBLICATIONS

International Search Report of Application No. PCT/IL05/01081 Dated Jan. 29, 2007.

(Continued)

*Primary Examiner* — Michael Peffley
*Assistant Examiner* — Daniel Fowler
(74) *Attorney, Agent, or Firm* — Pearl Cohen Zedek Latzer Baratz, LLP

(57) ABSTRACT

Devices, systems and methods for in-vivo cauterization. An autonomous in-vivo device may include a heating mechanism to cauterize in-vivo tissue. A system may include an autonomous in-vivo heating device having a heating mechanism to cauterize in-vivo tissue, and an in-vivo imaging device to acquire in-vivo images.

17 Claims, 4 Drawing Sheets

(56) References Cited

U.S. PATENT DOCUMENTS

| | | | |
|---|---|---|---|
| 4,483,341 A | | 11/1984 | Witteles |
| 4,979,518 A | | 12/1990 | Itoh et al. |
| 5,304,211 A | | 4/1994 | Israel et al. |
| 5,449,380 A | * | 9/1995 | Chin .............................. 607/105 |
| 5,586,982 A | * | 12/1996 | Abela ............................. 606/28 |
| 5,604,531 A | | 2/1997 | Iddan et al. |
| 5,993,378 A | | 11/1999 | Lemelson |
| 6,033,401 A | * | 3/2000 | Edwards et al. ................. 606/41 |
| 6,159,207 A | * | 12/2000 | Yoon ................................ 606/41 |
| 6,240,312 B1 | | 5/2001 | Alfano et al. |
| 2001/0035902 A1 | | 11/2001 | Iddan et al. |
| 2002/0103417 A1 | | 8/2002 | Gazdzinski |
| 2002/0109774 A1 | | 8/2002 | Meron et al. |
| 2003/0167000 A1 | * | 9/2003 | Mullick et al. ................. 600/424 |
| 2004/0106849 A1 | | 6/2004 | Cho et al. |
| 2004/0162501 A1 | | 8/2004 | Imran |

FOREIGN PATENT DOCUMENTS

| | | |
|---|---|---|
| JP | 4-109927 | 4/1992 |
| JP | 1992-144533 | 5/1992 |
| WO | WO 01/65995 | 9/2001 |

OTHER PUBLICATIONS

International Search Report of Application No. PCT/IL05/01299 Dated Aug. 10, 2006.

* cited by examiner

DEVICE, SYSTEM AND METHOD FOR IN-VIVO CAUTERIZATION

CROSS-REFERENCE TO RELATED APPLICATIONS

This application is a National Phase of PCT International Application No. PCT/IL2005/001081, International Filing Date Oct. 11, 2005, claiming priority from Israeli Patent Application No. 164501, filed Oct. 11, 2004, and claiming the benefit of U.S. Provisional Application No. 60/617,057, filed Oct. 12, 2004, each of which is hereby incorporated by reference herein in its entirety.

This application claims the benefit of U.S. Provisional Application No. 60/632,260, filed Dec. 2, 2004, which is hereby incorporated by reference herein in its entirety.

This application is a continuation of PCT International Application No. PCT/IL2005/000510, International Filing Date May 17, 2005, which is hereby incorporated by reference herein in its entirety.

FIELD OF THE INVENTION

The present invention relates to the field of in-vivo operations. More specifically, the present invention relates devices, systems and methods for performing in-vivo heating operations.

BACKGROUND OF THE INVENTION

Bleeding from sources in the gastrointestinal (GI) tract is common, and remains a major cause of morbidity and mortality. Internal bleeding may be treated using a wired endoscope; however, undergoing such penetrative treatment may be uncomfortable for the patient.

SUMMARY OF THE INVENTION

Some embodiments of the present invention may include, for example, devices, systems and methods for applying heat in-vivo, for example, to cauterize and/or coagulate tissue in-vivo.

In some embodiments, for example, an in-vivo heating device may be autonomous. In some embodiments, for example, the in-vivo heating device may be swallowable, e.g., a swallowable capsule which may be swallowed and naturally moved through the GI tract.

In some embodiments, for example, the in-vivo heating device may be controlled, externally-controlled or remotely-controlled, e.g., by an external operator.

In some embodiments, the in-vivo heating device may include an in-vivo imager. For example, the in-vivo imaging device may be implemented using an autonomous and/or swallowable device, e.g., capsule, having a heating unit and optionally an imager In some embodiments, for example, utilizing the in-vivo heating device may allow treatment of internal bleeding, e.g., to reduce re-bleeding rate, to reduce a need for surgery, and/or to reduce mortality due to internal bleeding. For example, the in-vivo heating device may be utilized to coagulate incidental abnormalities, e.g., angiodysplasias scattered throughout the small intestine. Some embodiments may allow treatment of gastrointestinal bleeding or neoplasia, for example, at hard-to-reach portions of the GI tract, e.g., the small intestine. Other advantages or benefits may be possible.

In some embodiments, for example, an autonomous in-vivo device may include a heating mechanism to cauterize in-vivo tissue.

In some embodiments, for example, the heating mechanism may include a heating element, may be pre-heated, may be electrically heated or pre-heated, and/or may be removable.

In some embodiments, for example, the in-vivo device may include a heating plate thermally connected to the heating element. The heating plate may be attached to at least a portion of a housing of the in-vivo device. A thermal conduit may connect the heating plate and the heating element.

In some embodiments, for example, the heating mechanism may include an electrical heating mechanism, a chemical heating mechanism, or other suitable mechanisms.

In some embodiments, for example, the heating mechanism may include a first compartment to store a first substance, e.g., calcium oxide, and a second compartment to store a second substance, e.g., water. A channel may be used to mix the first substance and the second substance; optionally, a switch may control an opening of the channel.

In some embodiments, for example, the in-vivo device may include multiple heating units.

In some embodiments, for example, the in-vivo device may include a controller to activate the heating mechanism in response to a triggering signal; a receiver to receive the triggering signal; an imager to acquire in-vivo images; a transmitter to transmit image data; an internal power source; one or more illumination source; an optical system; and/or other suitable components.

In some embodiments, for example, the in-vivo device may be autonomous and/or a swallowable capsule.

In some embodiments, for example, a system may include an autonomous in-vivo heating device having a heating mechanism to cauterize in-vivo tissue; and an in-vivo imaging device to acquire in-vivo images. The system may optionally include a cable to connect the in-vivo heating device and the in-vivo imaging device; and/or a motor to rotate the in-vivo heating device. In some embodiments, the in-vivo heating device may be activated based on data obtained by the in-vivo imaging device.

In some embodiments, for example, a method may include cauterizing a tissue in-vivo using an autonomous in-vivo heating device; activating in-vivo a heating mechanism of the in-vivo heating device; activating in-vivo the heating mechanism in response to a triggering signal; activating in-vivo the heating mechanism based on a location of the in-vivo heating device; mixing in-vivo, within the in-vivo heating device, a first substance and a second substance; and/or other suitable operations.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1:
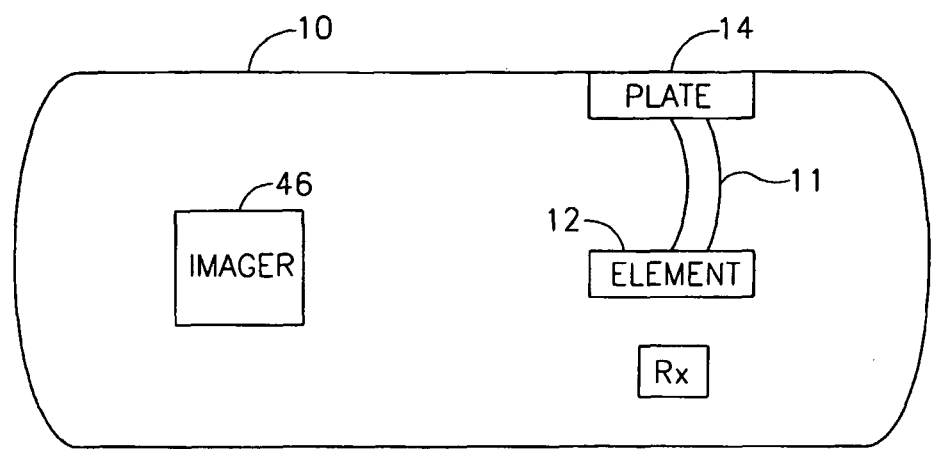
FIG. 1 is a schematic illustration of an in-vivo heating device according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention. Some embodiments of the present invention are directed to a typically swallowable in-vivo device, e.g., a typically swallowable in-vivo sensing or imaging device. Devices according to embodiments of the present invention may be similar to embodiments described in U.S. patent application Ser. No. 09/800,470, entitled "Device and System for In-vivo Imaging", filed on 8 Mar. 2001, published on Nov. 1, 2001 as United States Patent Application Publication Number 2001/0035902, and/or in U.S. Pat. No. 5,604,531 to Iddan et al., entitled "in-Vivo Video Camera System", and/or in U.S. patent application Ser. No. 10/046,541, filed on Jan. 16, 2002, published on Aug. 15, 2002 as United States Patent Application Publication Number 2002/0109774, all of which are hereby incorporated by reference. An external receiver/recorder unit, a processor and a monitor, e.g., in a workstation, such as those described in the above publications, may be suitable for use with some embodiments of the present invention. Devices and systems as described herein may have other configurations and/or other sets of components. For example, the present invention may be practiced using an endoscope, needle, stent, catheter, etc. Some in-vivo devices may be capsule shaped, or may have other shapes, for example, a peanut shape or tubular, spherical, conical, or other suitable shapes.

Some embodiments of the present invention may include, for example, a typically swallowable in-vivo device that may be used for heat applying procedures, e.g., gastro-intestinal hemostasis, for example, in the entire length of the gastrointestinal (GI) tract. In other embodiments, an in-vivo heating device need not be swallowable and/or autonomous, and may have other shapes or configurations. Some embodiments may be used in other body lumens, for example, blood vessels, the urinary tract, the reproductive tract, or the like. In some embodiments, the in-vivo device may optionally include a sensor, an imager, and/or other suitable components.

Embodiments of the in-vivo device are typically autonomous and are typically self-contained. For example, the in-vivo device may be or may include a capsule or other unit where all the components are substantially contained within a container, housing or shell, and where the in-vivo device does not require any wires or cables to, for example, receive power or transmit information. The in-vivo device may communicate with an external receiving and display system to provide display of data, control, or other functions. For example, power may be provided by an internal battery or a wireless receiving system.

Other embodiments may have other configurations and capabilities. For example, components may be distributed over multiple sites or units. Control information may be received from an external source.

In some embodiments, an in-vivo device may be used to heat a tissue in a body lumen. In some embodiments, for example, electrical power, e.g., provided by an internal battery, may be used to heat an in-vivo location or tissue. In some embodiments, non-electrical methods preformed by the in-vivo autonomous device may be used to heat. tissue, for example, thermal capacitance methods, a "heat brick" method, or the like.

FIG. 1 schematically illustrates an in-vivo heating device 10 in accordance with an embodiment of the invention. Device 10, for example, may be autonomous and/or may be implemented as a swallowable capsule. In some embodiments, device 10 may be or may include a heat-insulated capsule.

Device 10 may include, for example, an element 12 able to retain and release heat. Element 12 may be heated externally to a patient's body, for example, prior to swallowing or otherwise inserting device 10 into a patient's body. Element 12 may be heated outside the patient, for example, by plugging into a mains-powered heating element, or utilizing other heating sources. Element 12 may be removed from the heating source and inserted into device 10, which may be, for example, a thermally-insulated capsule.

Element 12 may retain its heat, for example, upon placement within inside device 10. Element 12 may discharge or release the retained heat in-vivo, for example, in response to a triggering signal or a triggering event, e.g., in response to an electrical signal from another component of device 10, in response to a wireless signal received by device 10 from an external transmitter or from another in-vivo device, in response to a determination that a pre-defined condition is met, in response to identification or visual identification of a certain location of a body lumen, based on localization data of device 10, when device 10 is in contact with or proximity to a bleeding point or bleeding area in-vivo, or the like.

In some embodiments, for example, heat may be released when device 10 is in contact with tissue intended for ablation, coagulation, cauterization, or other heat-related operations. For example, the heat may be released by enabling a thermo-conductive conduit 11 to allow passage of heat from element 12 to, for example, a plate 14 (e.g., a metal plate) on the surface of device 10.

Figure 4:
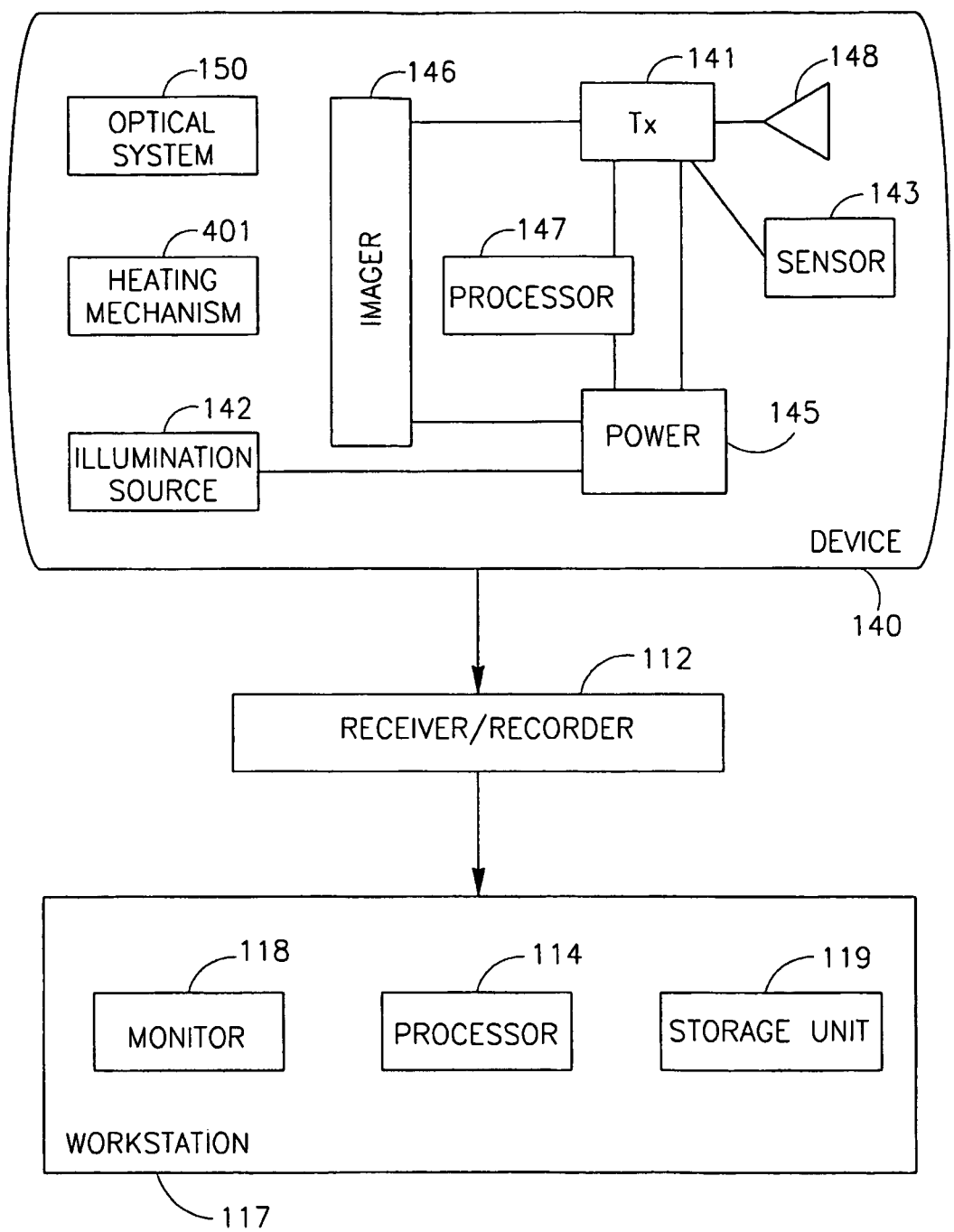
FIG. 4 is a schematic illustration of an in-vivo system according to an embodiment of the invention.

In some embodiments, optionally, device 10 may further include an in-vivo imager 46 able to acquire in-vivo images, one or more illumination source(s) able to provide illumination in-vivo, an optical system able to focus light onto the imager, an in-vivo sensor, a transmitter able to transmit image data or other sensed data, a receiver 16 able to receive signals (e.g., a wireless signal indicating a command to release heat in-vivo), an antenna, a power source, and/or other suitable components, e.g., which may be similar to components shown in FIG. 4 herein. In some embodiments, the transmitter and/or the receiver 16 may utilize wired or wireless communications, e.g., using Radio Frequency (RF) signals, Infra Red (IR) signals, microwave signals, or the like.

Device 10 may be, for example, capsule-shaped, may be swallowed, and may pass (e.g., passively) through the entire GI tract, pushed along, for example, by natural peristalsis. Device 10 may have other suitable shapes or dimensions, for example, suitable for being inserted into and passing through a body lumen or cavity, e.g., spherical, oval, cylindrical, or the like. In some embodiments, device 10, or one or more components of device 10, may be attached to, or affixed onto, or included in an instrument that may be inserted into body lumens and cavities, for example, an endoscope, laparoscope, stent, needle, catheter, or the like.

In some embodiments, device 10 may utilize non-electrical methods for ablation, coagulation, cauterization, or other heat-related operations. For example, in some embodiments, mechanical methods may be used, e.g., utilizing one or more clips, bands, clamps, or the like. In some embodiments, chemical methods may be used, for example, utilizing calcium oxide (CaO2) heating, non-thermal tissue injury (e.g., silver nitrate), alum, and/or cryo (e.g., chemical or gas discharge).

Figure 2:
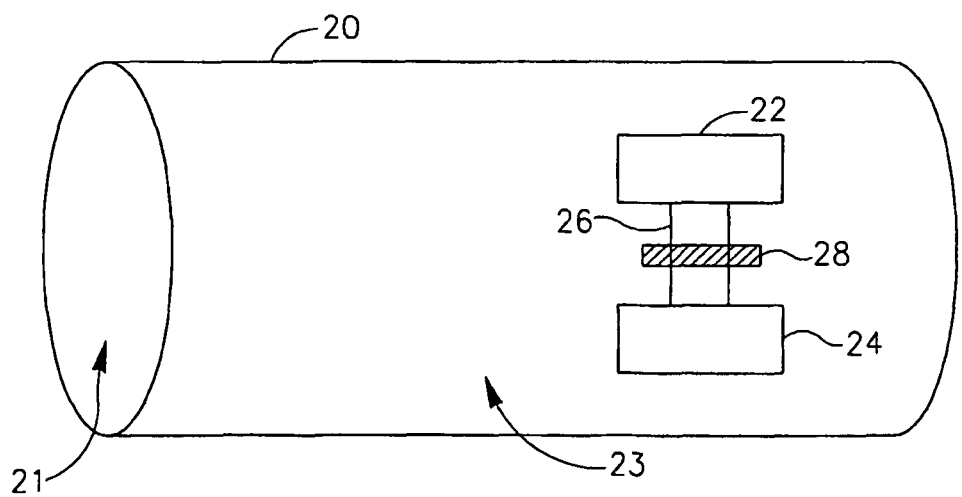
FIG. 2 is a schematic illustration of an in-vivo heating device according to another embodiment of the invention.

FIG. 2 schematically illustrates an in-vivo heating device 20 in accordance with another embodiment of the invention. Device 20 may include multiple compartments (e.g., tanks, chambers or repositories), for example, a first compartment 22 containing calcium oxide, and a second compartment 24 containing water. Other suitable substances may be used. Device 20 may further include a channel 26 which may allow or disallow mixing of the content of compartments 22 and 24, e.g., the mixing of the calcium oxide with the water. Device 20 may further include a switch 28, e.g., a controllable switch which may be controlled using a signal, for example, a wired signal, a wireless signal, a Radio Frequency (RF) signal, a microwave signal, an ultrasound signal, a magnetic signal, or the like. In response to the signal, switch 28 may control the channel 26, e.g., to allow or disallow mixing of the calcium oxide with the water.

In some embodiments, device 20 may include a coagulation portion, for example, a thermally-conductive element 21, which may include, e.g., a metal plate inserted into the shell of device 20 and able to heat up and coagulate the tissue. Device 20 may include a thermally-insulated portion 23, for example, formed of plastic or other materials (e.g., insulating materials), which may prevent the heat within device 20 from damaging adjacent tissue which may not require coagulation.

In some embodiments, device 20 may obtain and/or transmit information (e.g., substantially real-time information) about the source and position or location of a bleeding point in-vivo, and/or the position or location or orientation of the coagulating portion of device 20. Optionally, coagulation may be performed in-vivo based on the information obtained and/or transmitted by device 20.

In some embodiments, the weight or mass of calcium oxide in compartment 22, and/or the volume of water in compartment 24, may be adjusted, for example, to produce a desired (e.g., efficient, near-optimal or optimal) coagulative effect or other effect. For example, too little heat on the bleeding point may not coagulate the tissue, whereas too much heat may cause injury, e.g., full thickness injury. In some embodiments, device 20 may produce and/or utilize electrocautery of approximately 10 to 20 joules of energy, e.g., to stop bleeding; other suitable values or ranges may be used.

In some embodiments, mixing the water and the calcium oxide may be performed, for example, utilizing a waterless method or unit, e.g., a membrane allowing tissue water to contact the calcium oxide. In some embodiments methods or units for steam handling may be used, for example, a blowhole safety valve, which may be safely sited (e.g., centrally on a dome of in-vivo device 20), a condenser, controlled mixing to avoid steam formation, a tight seal on device 20 which may be resistant to resulting pressure, or the like.

In some embodiments, optionally, a radio-controlled or otherwise remote-controlled heat switch may be used, e.g., to commence and/or terminate heating. For example, a thermal non-conductive material, or an insulating material, may be used, e.g., inserted into a pathway (e.g., conduit 11, or channel 26) in response to a control signal. For example, a piece of plastic may be passed or inserted into a thermally-conductive pathway, e.g., conduit 26. Other suitable materials may be used, for example, an inert gas, and other suitable operations or components may be used to commence and/or terminate the heating effect.

In some embodiments, it may be possible to calculate the amount of heat produced per mass of calcium oxide and water. In some embodiments, the amount of materials needed, for example, to achieve near-optimal therapy may depend on the design characteristics of the in-vivo device 20, e.g., dimensions and/or functions of the in-vivo device 20 in various specific implementations.

In some embodiments, mixing the water and the calcium oxide in-vivo, e.g., within device 20, may result in an exothermic reaction and/or may generate heat; for example, a substantial temperature increase may be obtained, and calcium hydroxide may be formed. In one embodiment, for example, a temperature of approximately 100 degrees centigrade may be obtained using hot water and/or boiled water. In one embodiment, for example, a three-to-one ratio of calcium oxide to water may be used to produce a heating effect; other suitable ratios may be used.

In some embodiments, for example, device 20 may include a swallowable capsule having a length of approximately 33 millimeters and a width of approximately 11 millimeters; other suitable dimensions, sizes and/or shapes may be used. In some embodiments, for example, device 20 or portions thereof may be formed of aluminum; other suitable materials may be used to form device 20 and/or to produce heat therein, for example, alum, silver nitrate sticks, sodium, or the like.

In some embodiments, mixing in-vivo a relatively small amount of calcium oxide and water may produce heat having a relatively high temperature which may, in one embodiment, reach a boiling point. This may allow in-vivo thermo-coagulation which may be similar, for example, to coagulation obtained from twenty two-seconds pulses of using a heater probe or a bipolar probe. Other heat levels or energy levels may be used. Other suitable chemicals or substances may be mixed, e.g., at substantially body temperature or room temperature, to allow in-vivo heating operations.

In some embodiments, multiple sets or complexes of compartments may be used. For example, device 20 may include six sets, each set having a calcium oxide compartment 22, a water compartment 24, and a channel 26; optionally, each set may be operatively connected through a conduit 11 to a heating plate 14. For example, multiple (e.g., six) heating plates may be mounted on various areas of the surface of device 20. In some embodiments, each of these sets may be activated, deactivated and/or controlled separately, selectively or individually, e.g., in response to a control signal and/or when a portion of device 20 is in contact with a bleeding abnormality. Other numbers of sets or complexes may be used; for example, in some embodiments, multiple types of heating mechanisms may be incorporated into device 20, e.g., a thermo-chemical mechanism, an electrical mechanism, or the like.

In some embodiments, device 20 may incorporate or include components of an in-vivo heating device and/or components of an in-vivo imaging device and/or an in-vivo sensing device. In other embodiments, multiple in-vivo devices may be used, e.g., substantially simultaneously; for example, a first in-vivo device may be used for imaging a body lumen, and a second in-vivo device may be used for coagulating or cauterizing a portion of a body lumen, e.g., the imaged body lumen. Optionally, one or more one or more of the in-vivo devices may use electro-stimulation to urge an in-vivo device forwards or backwards and/or sideways, so that it may make contact a bleeding point. Additionally or alternatively, electro-stimulation may be used to cause a bleeding lesion to be pressed against a coagulating zone (e.g., portion 21 of device 20) prior to thermo-coagulation, e.g., to produce a more efficient effect.

In some embodiments, optionally, device 20 may further include an in-vivo imager able to acquire in-vivo images, one or more illumination source(s) able to provide illumination in-vivo, an optical system able to focus light onto the imager, an in-vivo sensor, a transmitter able to transmit image data or other sensed data, a receiver able to receive signals (e.g., a wireless signal indicating a command to release heat in-vivo), an antenna, a power source, and/or other suitable components, e.g., which may be similar to components shown in FIG. 4 herein. In some embodiments, the transmitter and/or the receiver may utilize wired or wireless communications, e.g., using Radio Frequency (RF) signals, Infra Red (IR) signals, microwave signals, or the like.

Figure 3:
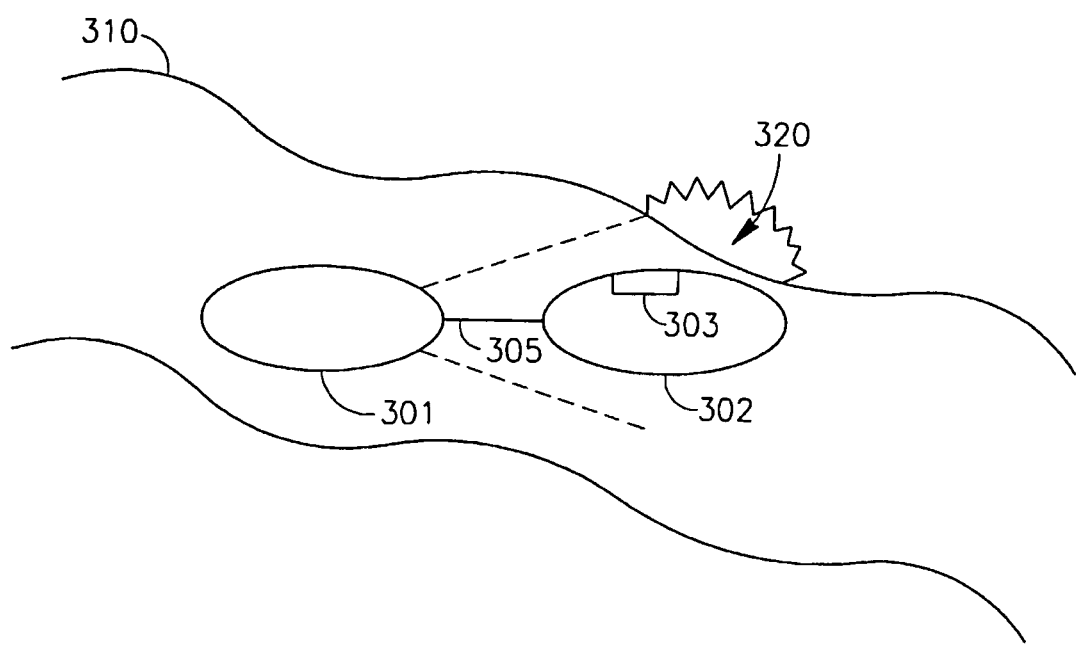
FIG. 3 is a schematic illustration of a set of multiple in-vivo devices according to an embodiment of the invention.

FIG. 3 schematically illustrates a set of multiple in-vivo devices in accordance with an embodiment of the invention. An in-vivo imaging device 301 and an in-vivo coagulating device 302 may be inserted into a patient's body, e.g., one after the other or substantially simultaneously, and may pass through a body lumen 310. The in-vivo imaging device 301 may image, for example, a bleeding portion 320 of body lumen 310. The in-vivo coagulating device may cauterize the bleeding portion 310, e.g., using a heating plate 303 when in-vivo coagulating device 302 is in contact with bleeding portion 310.

In some embodiments, multiple (e.g., two) in-vivo devices may be used; for example, a first in-vivo device (e.g., device 301) may include an imager for imaging a second in-vivo device (e.g., device 302) used for coagulation or cauterization. Optionally, a spacer, a thread, a coaxial cable, a cable, or other connector 305 may connect or join the multiple in-vivo devices. This may allow, for example, the coagulation or thermo-coagulation to take place under direct vision of the in-vivo imaging device 302.

In some embodiments, the in-vivo coagulating device 302 and/or the in-vivo imaging device 301 may be rotated relative to each other, for example, such that the bleeding portion 320 may be brought into contact with heating plate 303 or the active area on the surface of the in-vivo coagulating device 302. This may be performed, for example, by linking the two in-vivo devices together, e.g., using connector 305 (e.g., a coaxial cable) which may optionally be rotated by a motor. In one embodiment, the in-vivo coagulation 302 device and the in-vivo imaging device 301 may have a similar masses, and one or more expandable wings, or a keel like structure, may be attached to one of the in-vivo devices, e.g., to reduce a possible tendency of the in-vivo imaging device 301 to rotate relative to the in-vivo coagulating device 302 if a motor rotates the in-vivo coagulation device 302. Other sets or combinations of in-vivo devices may be used.

FIG. 4 schematically illustrates an in-vivo system in accordance with some embodiments of the present invention. One or more components of the system may be used in conjunction with, or may be operatively associated with, the devices and/or components described herein or other in-vivo devices in accordance with embodiments of the invention.

In some embodiments, the system may include a device 140 having a sensor, e.g., an imager 146, one or more illumination sources 142, a power source 145, and a transmitter 141. In some embodiments, device 140 may be implemented using a swallowable capsule, but other sorts of devices or suitable implementations may be used. Outside a patient's body may be, for example, an external receiver/recorder 112 (including, or operatively associated with, for example, one or more antennas, or an antenna array), a storage unit 119, a processor 114, and a monitor 118. In some embodiments, for example, processor 114, storage unit 119 and/or monitor 118 may be implemented as a workstation 117, e.g., a computer or a computing platform.

Transmitter 141 may operate using radio waves; but in some embodiments, such as those where device 140 is or is included within an endoscope, transmitter 141 may transmit/receive data via, for example, wire, optical fiber and/or other suitable methods. Other known wireless methods of transmission may be used. Transmitter 141 may include, for example, a transmitter module or sub-unit and a receiver module or sub-unit, or an integrated transceiver or transmitter-receiver.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit information. In some embodiments, device 140 may be autonomous and non-remote-controllable; in another embodiment, device 140 may be partially or entirely remote-controllable.

In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

In some embodiments, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 in device 140 may be operationally connected to transmitter 141. Transmitter 141 may transmit images to, for example, external transceiver or receiver/recorder 112 (e.g., through one or more antennas), which may send the data to processor 114 and/or to storage unit 119. Transmitter 141 may also include control capability, although control capability may be included in a separate component, e.g., processor 147. Transmitter 141 may include any suitable transmitter able to transmit image data, other sensed data, and/or other data (e.g., control data) to a receiving device. Transmitter 141 may also be capable of receiving signals/commands, for example from an external transceiver. For example, in some embodiments, transmitter 141 may include an ultra low power Radio Frequency (RF) high bandwidth transmitter, possibly provided in Chip Scale Package (CSP).

In some embodiment, transmitter 141 may transmit/receive via antenna 148. Transmitter 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transmitter 141 may include a receiver which may receive signals (e.g., from outside the patient's body), for example, through antenna 148 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

In some embodiments, power source 145 may be internal to device 140, and/or may not require coupling to an external power source, e.g., to receive power. Power source 145 may provide power to one or more components of device 140 continuously, substantially continuously, or in a non-discrete manner or timing, or in a periodic manner, an intermittent manner, or an otherwise non-continuous manner. In some embodiments, power source 145 may provide power to one or more components of device 140, for example, not necessarily upon-demand, or not necessarily upon a triggering event or an external activation or external excitement.

Optionally, in some embodiments, transmitter 141 may include a processing unit or processor or controller, for example, to process signals and/or data generated by imager 146. In another embodiment, the processing unit may be implemented using a separate component within device 140, e.g., controller or processor 147, or may be implemented as an integral part of imager 146, transmitter 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transmitter 141, and may be implemented, for example, using an ASIC.

In some embodiments, imager 146 may acquire in-vivo images continuously, substantially continuously, or in a non-discrete manner, for example, not necessarily upon-demand, or not necessarily upon a triggering event or an external activation or external excitement; or in a periodic manner, an intermittent manner, or an otherwise non-continuous manner.

In some embodiments, transmitter 141 may transmit image data continuously, or substantially continuously, for example, not necessarily upon-demand, or not necessarily upon a triggering event or an external activation or external excitement; or in a periodic manner, an intermittent manner, or an otherwise non-continuous manner.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optional optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminated light, and/or performing other light processing operations.

In some embodiments, illumination source(s) 142 may illuminate continuously, or substantially continuously, for example, not necessarily upon-demand, or not necessarily upon a triggering event or an external activation or external excitement. In some embodiments, for example, illumination source(s) 142 may illuminate a pre-defined number of times per second (e.g., two or four times), substantially continuously, e.g., for a time period of two hours, four hours, eight hours, or the like; or in a periodic manner, an intermittent manner, or an otherwise non-continuous manner.

In some embodiments, the components of device 140 may be enclosed within a housing or shell, e.g., capsule-shaped, oval, or having other suitable shapes. The housing or shell may be substantially transparent or semi-transparent, and/or may include one or more portions, windows or domes which may be substantially transparent or semi-transparent.

For example, one or more illumination source(s) 142 within device 140 may illuminate a body lumen through a transparent or semi-transparent portion, window or dome; and light reflected from the body lumen may enter the device 140, for example, through the same transparent or semi-transparent portion, window or dome, or, optionally, through another transparent or semi-transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to external receiver/recorder 112. Other constant and/or variable capture rates and/or transmission rates may be used.

Typically, the image data recorded and transmitted may include digital color image data; in alternate embodiments, other image formats (e.g., black and white image data) may be used. In some embodiments, each frame of image data may include 256 rows, each row may include 256 pixels, and each pixel may include data for color and brightness according to known methods. For example, a Bayer color filter may be applied. Other suitable data formats may be used, and other suitable numbers or types of rows, columns, arrays, pixels, sub-pixels, boxes, super-pixels and/or colors may be used.

Optionally, device 140 may include one or more sensors 143, instead of or in addition to a sensor such as imager 146. Sensor 143 may, for example, sense, detect, determine and/or measure one or more values of properties or characteristics of the surrounding of device 140. For example, sensor 143 may include a pH sensor, a temperature sensor, an electrical conductivity sensor, a pressure sensor, or any other known suitable in-vivo sensor.

In some embodiments, device 140 may optionally include one or more in-vivo heating mechanisms 401, for example, a thermal heating mechanism, a mechanical heating mechanism, an electrical heating mechanism, an electro-thermal heating mechanism, a chemical heating mechanism, a removable heating mechanism, a non-removable heating mechanism, a heater, a heating unit, a heat-retaining element, a rechargeable or non-rechargeable heating mechanism, a mechanism having a heating plate or heating portion, a thermal coagulation mechanism, or the like. Heating mechanism 401 may, for example, perform in-vivo ablation, in-vivo coagulation, in-vivo cauterization, or other in-vivo heat-related operations.

Although portions of the discussion herein may relate to an imager or an image sensor, embodiments of the invention are not limited in this regard; such imager or image sensor may include, for example, a detector, a sensor, a photodiode, a florescence device, an electrochemical sensing device, a magnetic field sensing device, a spectrophotometer, an image sensor, a Charge Coupled Device (CCD) camera or imager, a Complementary Metal Oxide Semiconductor (CMOS) camera or imager, a digital camera, a stills camera, a video camera, a light sensor; a device capable of detecting or sensing one or more colors, intensities, hues, brightness, contrast, and/or other parameters or characteristic; a device sensitive to one or more colors or able to detect one or more colors; a device capable of detecting one or more color changes; a device sensitive to color changes; or the like.

Figure 5:
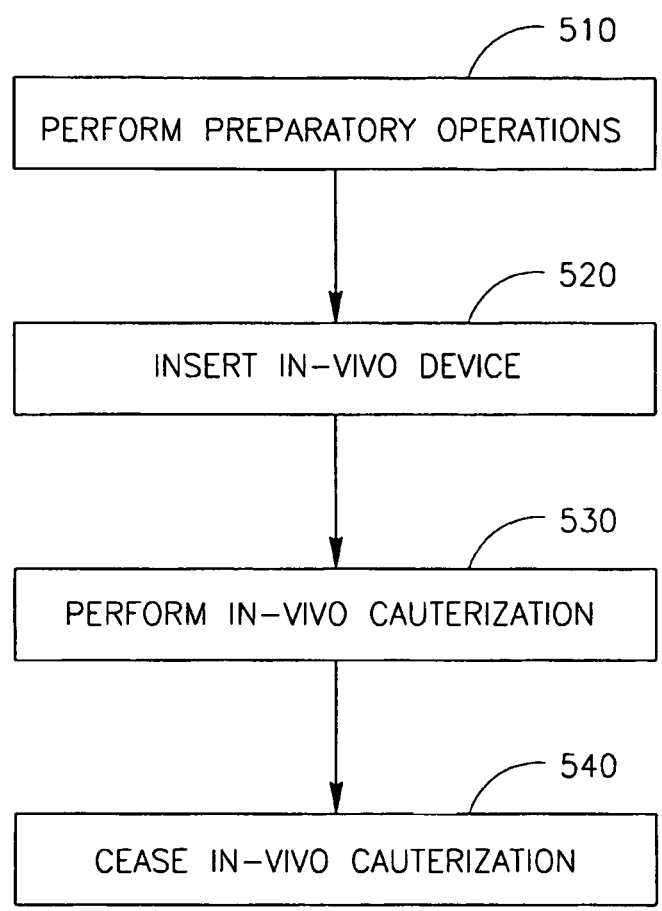
FIG. 5 is a flow-chart of a method of in-vivo cauterization according to an embodiment of the invention.

FIG. 5 is a flow-chart of a method of in-vivo cauterization in accordance with some embodiments of the invention. The method may be used, for example, in conjunction with one or more components, devices and/or systems described herein, and/or other suitable in-vivo devices and/or systems.

As indicated at box 510, the method may optionally include, for example, performing one or more preparatory operations. In one embodiment, for example, a heat-retaining element may be heated and inserted into an in-vivo device. In another embodiment, for example, one or more compartments in the in-vivo device may be filled with one or more substances able to release heat, e.g., upon mixture or when certain conditions are met.

As indicated at box 520, the method may include, for example, inserting the in-vivo device into a patient's body. For example, an in-vivo heating device may be inserted, e.g., swallowed.

As indicated at box 530, the method may include, for example, performing ablation, coagulation, cauterization, or other heat-related operations in-vivo. This may include, for example, activating a heating element or heating mechanism, mixing two or more substances, or other operations to generate heat and/or release heat. In some embodiments, the heat-related operations may be performed in response to a triggering event, a triggering signal, when a pre-defined condition is met, when the in-vivo device reaches a certain location, or the like.

As indicated at box 540, the method may optionally include, for example, terminating or ceasing heating operations. This may include, for example, deactivating a heating element or heating mechanism, disallowing multiple substances to mix, closing a channel connecting multiple compartments, disconnecting or closing a heat-transferring conduit, or the like.

Other suitable operations of sets of operations may be used.

Various aspects of the various embodiments disclosed herein are combinable with the other embodiments disclosed herein.

A device, system and method in accordance with some embodiments of the invention may be used, for example, in conjunction with a device which may be inserted into a human body. However, the scope of the present invention is not limited in this regard. For example, some embodiments of the invention may be used in conjunction with a device which may be inserted into a non-human body or an animal body.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A system comprising:
    an autonomous in-vivo heating device comprising a swallowable capsule having a housing, said housing containing:
        a heating mechanism to cauterize in-vivo tissue, wherein the heating mechanism comprises a heating element and a heating plate exposed on the surface of the housing, wherein the heating element and the heating plate are thermally connected by a thermo-conductive conduit to allow passage of heat from the heating element to the heating plate, thereby heating the heating plate for cauterization of tissue in-vivo;
    an autonomous, swallowable in-vivo imaging device to capture in-vivo images;
    a cable to connect the in-vivo heating device and the in-vivo imaging device; and
    a motor to rotate the in-vivo heating device relative to the in-vivo imaging device.

2. The system of claim 1, wherein the in-vivo heating device is activated based on data obtained by the in-vivo imaging device.

3. The system of claim 1, wherein the heating element is electrically heated.

4. The system of claim 1, wherein the heating element is removable.

5. The system of claim 1, wherein the heating plate is exposed on a portion of the housing of the in-vivo heating device.

6. The system of claim 1, wherein the heating mechanism comprises an electrical heating mechanism or a chemical heating mechanism.

7. The system of claim 6, wherein the heating mechanism comprises a chemical heating mechanism comprising: a first compartment to store a first substance; and a second compartment to store a second substance.

8. The system of claim 7, further comprising: a channel to mix the first substance and the second substance.

9. The system of claim 8, further comprising: a switch to control an opening of the channel.

10. The system of claim 7, wherein the first substance comprises calcium oxide, and wherein the second substance comprises water.

11. The system of claim 1, wherein the heating mechanism comprises a plurality of heating units.

12. The system of claim 1, further comprising: a controller to activate the heating mechanism in response to a triggering signal.

13. The system of claim 12, further comprising: a receiver to receive the triggering signal.

14. A method comprising: cauterizing a tissue in-vivo using the autonomous in-vivo heating device as claimed in claim 1.

15. The method of claim 14, comprising: activating in-vivo a heating mechanism of the in-vivo heating device.

16. The method of claim 15, comprising: activating in-vivo the heating mechanism in response to a triggering signal or based on a location of the in-vivo heating device.

17. The method of claim 14, comprising: mixing in-vivo, within the in-vivo heating device, a first substance and a second substance.

* * * * *